(12) United States Patent
Piasio et al.

(10) Patent No.: US 10,458,974 B2
(45) Date of Patent: Oct. 29, 2019

(54) UNIVERSAL TESTING SYSTEM FOR QUANTITATIVE ANALYSIS

(71) Applicant: Optimum Imaging Diagnostics LLC, Scarborough, ME (US)

(72) Inventors: Roger Piasio, Cumberland-Foreside, ME (US); Andrew Wheeler, Hollis Center, ME (US); Wesley Cowperthwaite, Windham, ME (US)

(73) Assignee: OPTIMUM IMAGING DIAGNOSTICS LLC, Scarborough, ME (US)

( * ) Notice: Subject to any disclaimer, the term of this patent is extended or adjusted under 35 U.S.C. 154(b) by 154 days.

(21) Appl. No.: 15/710,223

(22) Filed: Sep. 20, 2017

(65) Prior Publication Data
US 2018/0356393 A1 Dec. 13, 2018

Related U.S. Application Data

(60) Provisional application No. 62/517,441, filed on Jun. 9, 2017.

(51) Int. Cl.
*G01N 33/50* (2006.01)
*G01N 33/49* (2006.01)
(Continued)

(52) U.S. Cl.
CPC ............ *G01N 33/492* (2013.01); *B01L 3/502* (2013.01); *B01L 3/5023* (2013.01);
(Continued)

(58) Field of Classification Search
None
See application file for complete search history.

(56) References Cited

U.S. PATENT DOCUMENTS

| 4,098,876 A | 7/1978 | Piasio et al. |
| 4,378,344 A | 3/1983 | Zahradnik et al. |

(Continued)

FOREIGN PATENT DOCUMENTS

WO 2017087831 A1 5/2017

OTHER PUBLICATIONS

O'dell; "Fast and Convenient Vitamin Deficiency Test"; VitaScan; 2017; 3 pages.
(Continued)

*Primary Examiner* — Erik B Crawford
(74) *Attorney, Agent, or Firm* — Hayes Soloway PC

(57) ABSTRACT

A cassette is disclosed that permits, with an instrument, quantitative analysis to be performed at the moment of sample testing without additional steps to the end user. The cassette includes a calibration strip and a sample strip. The calibration strip contains known quantities of analyte, from which a calibration curve can be created and applied to the analysis of the sample strip. The disclosed cassette can utilize light transmission or light reflectance techniques. The cassette may include a separate wash port for rapid washing of a high background sample. The disclosed cassette may perform diagnostic tests for humans, animals, environmental sample, and/or food samples. In some cases, the disclosed devices and techniques may be used to monitor efficacy of drug therapy and patient compliance with respect to physician-prescribed medication in a point of care setting.

20 Claims, 7 Drawing Sheets

(51) Int. Cl.
  *B01L 3/00* (2006.01)
  *G01N 33/558* (2006.01)
  *A61B 5/15* (2006.01)
  *G01N 21/84* (2006.01)

(52) U.S. Cl.
  CPC ...... *G01N 33/558* (2013.01); *A61B 5/150022* (2013.01); *B01L 2200/0621* (2013.01); *B01L 2300/0867* (2013.01); *G01N 21/8483* (2013.01); *G01N 2021/8488* (2013.01)

(56) References Cited

U.S. PATENT DOCUMENTS

| | | | |
|---|---|---|---|
| 4,981,786 A * | 1/1991 | Dafforn | G01N 33/5302 422/412 |
| 5,877,028 A | 3/1999 | Chandler et al. | |
| 7,358,099 B2 | 4/2008 | Piasio et al. | |
| 8,354,245 B2 | 1/2013 | Piasio et al. | |
| 9,445,749 B2 | 9/2016 | Erickson et al. | |
| 9,556,472 B2 | 1/2017 | Piasio et al. | |
| 2002/0173050 A1 * | 11/2002 | DiNello | B01L 3/5023 436/518 |
| 2006/0008847 A1 * | 1/2006 | Ramel | B01L 3/5023 435/7.1 |
| 2007/0020768 A1 * | 1/2007 | Rundstrom | G01N 33/543 436/514 |
| 2009/0155921 A1 * | 6/2009 | Lu | G01N 21/274 436/164 |
| 2009/0257915 A1 | 10/2009 | Dinello et al. | |
| 2009/0258343 A1 * | 10/2009 | Reiter | G01N 33/558 435/5 |
| 2010/0035245 A1 | 2/2010 | Stiene et al. | |
| 2010/0167264 A1 | 7/2010 | Lee | |
| 2013/0189794 A1 * | 7/2013 | Emeric | B01L 3/50273 436/501 |
| 2013/0224771 A1 | 8/2013 | McDade et al. | |
| 2015/0064800 A1 * | 3/2015 | Chance | G01N 33/6863 436/501 |
| 2015/0244852 A1 | 8/2015 | Erickson et al. | |

OTHER PUBLICATIONS

Hermanson; "Enzyme Modification and Conjugation"; Bioconjugate Techniques; 2013; p. 963-965; Third Edition.

* cited by examiner

UNIVERSAL TESTING SYSTEM FOR QUANTITATIVE ANALYSIS

CROSS REFERENCE TO RELATED APPLICATION

This application claims priority from U.S. Provisional Application Ser. No. 62/517,441, filed Jun. 9, 2017, the contents of which are incorporated by reference herein.

BACKGROUND

Blood testing represents a significant majority of human medical testing needs. Coupled with the growing need for physicians to monitor efficacy of drug therapy, there is also a growing need and demand for a portable quantitative point of care (POC) testing system. POC testing is projected to reach 22 billion dollars sometime in 2022. Typically, a large majority of blood tests are done in a central laboratory with expensive and complicated robotics. In order for many blood tests to reach the POC market the tests will, at a minimum, have to be simple to do and provide the same precision and accuracy as generated by the central laboratories. Moderately complex (for example, ELISA) technology has allowed physicians to avoid the central laboratory in some cases. However, these technologies are not generally available to Clinical Laboratory Improvement Amendments (CLIA) licensed POC physicians and are typically not subject to the Food and Drug Administration (FDA) CLIA waved status and therefore not available for point of care testing. Previous efforts to provide quantitative point of care testing have relied on pre-made calibration curves set at the date of manufacture and transmitted via barcode or chip device sold with the disposable test. However, pre-made calibration curves have significant limitations.

SUMMARY

The disclosed techniques can overcome issues with previously used techniques as a sample with an analyte of interest is run concurrently with a calibration strip that includes different concentrations of the analyte of interest being measured in the sample strip or a control analyte (i.e., an analyte that is distinct from the analyte of interest), while also utilizing the same binding agents. Any minor instability of the detector binding agent is thus applicable to the same degree on the construct of the calibration curve and the patient sample. In other words, the disclosed system is self-correcting and capable of producing repeatable and accurate results.

Various devices and methods of quantitative and qualitative analysis are described herein. Specifically, a cassette is disclosed that includes an 'on-board' calibrator. The cassette includes, in many cases, a lateral flow strip for calibration and a lateral flow strip for a sample. The lateral flow strips are formed of porous membranes which permit capillary motion of fluid. The "calibration strip" includes at least two and, in some cases, three, four, or more regions with known concentrations of an analyte (either the analyte of interest in the sample or a control analyte). To use the cassette for analysis, a sample is deposited on the "sample strip" and a chase fluid is supplied to both the sample strip and the calibration strip. The chase fluid releases a conjugate substance from pads in contact with the sample strip and the calibration strip and the conjugate substance then travels up the strips. The conjugate substance is a binding partner to the analyte of interest and may comprise or consist of a marker. On the calibration strip, the conjugate substance encounters and binds with the analyte present. Once bound to the analyte (either directly or indirectly via a distinct binding partner), the marker emits a signal, which is directly proportional to the amount of analyte present. The signals that develop on the calibration strip are then interpreted optically by an instrument to generate a calibration curve which is used to calculate or interpret the concurrent signal that develops on the sample strip. The disclosed cassettes may be compatible with an instrument capable of interpreting images either through light transmission or light reflectance. In embodiments where increased sensitivity is desired, light transmission can be used.

The disclosed cassettes can be configured to measure any desired analyte of interest. For example, the cassettes can be configured to measure antigens, antibodies, hormones, proteins, receptors, DNA, RNA, enzymes, pharmaceutical substances, and/or environmental pollutants. Appropriate binding partners and/or markers can be selected based on the selected analyte of interest and/or control analyte and used to create an appropriate calibration strip and sample strip.

In one particular example embodiment, a cassette is designed to measure an antigen of interest. The calibration strip for this cassette includes known concentrations of the antigen and an antibody immunologically bound to the antigen. In this example embodiment, the cassette includes a conjugate pad with marker (for example, gold particles). When chase fluid is introduced, the marker is reconstituted and travels to and bind with the antigen bound to the antibody. On the sample strip, the sample mixes and together with the chase fluid reconstitutes the marker (in this example, colloidal gold detector particles) and moves onto a porous membrane. If antigen is present, a signal develops.

In a different example embodiment, a cassette is designed to measure an antigen of interest and the calibration strip includes known concentrations of an antigen bound to a marker. In this example embodiment, the conjugate pad includes antibodies which travel to and bind with the antigen bound to the marker when chase fluid is introduced. The cassettes disclosed herein may include a calibration strip and a sample strip with numerous possible combinations of suitable binding partners and/or markers for particular analytes of interest. Although antibodies and antigens are discussed in detail, the subject disclosure is not intended to be so limited. For example, sample and calibration strips that include analytes such as hormones, proteins, vitamins, enzymes, DNA, RNA, pharmaceutical substances, and/or environmental pollutants are all within the scope of the subject disclosure.

Surprisingly, the disclosed cassettes with "on-board" calibration features are able to distribute fluid, sample, binding agents and/or markers up two lateral flow strips evenly and with inconsequential variation. Furthermore, the disclosed cassettes are able to produce a robust and stable calibration curve from the calibration strip and accurately report an unknown quantitative result from the sample strip.

DETAILED DESCRIPTION

Testing devices, namely cassettes, are disclosed that provide "on-board" calibration functionality. In particular, the disclosed cassettes include a calibration strip and a sample strip, each formed of a porous material that permits fluid to flow therethrough using capillary force. The calibration strip contains known quantities of analyte, from which a calibration curve can be created and applied to the analysis of the sample strip. The cassette may include a separate wash port for rapid washing of a high background sample.

The cassette produces a signal, which can be read using light transmission or light reflectance techniques. The disclosed cassettes can be used in diagnostic tests for humans, animals, environmental sample, and/or food samples. If desired, the disclosed devices and techniques may be used to monitor efficacy of drug therapy and/or patient compliance with respect to physician-prescribed medication in a point of care (POC) setting. Details regarding construction of the cassette, calibration strip, and sample strip are described below in detail, along with related methods of use.

Cassette

FIG. 1 shows a perspective view of an example cassette 100 that includes a calibration strip 7 and a sample strip 2, in accordance with some example embodiments. As shown in FIG. 1, cassette 100 includes a substantially rigid housing having a top portion 1 and a bottom portion 8. Top portion 1 and bottom portion 8 of the housing may, in some embodiments, interconnect upon being pushed together to form a press fit or friction fit and remain mechanically secured together without adhesives. In some embodiments, top housing 1 and bottom housing 8 may include clamping regions 6 designed to form a press fit with the opposing housing. In some embodiments, cassette 100 includes at least one, at least, two, at least three, at least four, at least five, or at least six clamping regions 6.

FIG. 1 illustrates a cassette 100 with a sample strip 2 and a calibration strip 7. Within the cassette 100, fluid port 5 contacts both sample strip 2 and calibration strip 7. Cassette 100 also includes a sample port 4 into which sample can be introduced before traveling through sample strip 2. Sample port 4 is not in fluid communication with calibration strip 7. In some embodiments, cassette 100 includes a wash port 3, which may be used to provide additional wash for high background samples (for example, hemolyzed blood or pigmented samples). When present, wash port 3 is in fluid communication with sample strip 2 but not necessarily in fluid communication with calibration strip 7.

FIG. 2 shows an exploded view of the exemplary cassette 100 shown in FIG. 1. In particular, fluid pad 5, calibration strip 7, and sample strip 2 are more clearly visible and features of clamping regions 6 are shown. For example, FIG. 2 shows an example embodiment where the bottom portion 8 of the housing includes two arms 6A that clamp onto corresponding recessed areas 6B of the top portion 1 of the housing. In the example embodiment shown in FIG. 2, the top portion 1 of the housing includes four arms 6C that clamp onto corresponding recessed areas 6D of the bottom portion 8 of the housing.

FIG. 3 shows a bottom view of the exemplary cassette 100 shown in FIG. 1. As shown in FIG. 3, the bottom portion 8 of the housing may include a positioning groove 9, which allows the cassette 100 to be easily positioned for reading and analysis. The bottom portion 8 of the housing may also include a flow strip light guide port 10 positioned underneath the calibration strip 7, which may be used for transmission-based detection methods. In some example embodiments, a barcode 11 may be placed on cassette 100, as shown in FIG. 3. A sample volume analysis port 12 may also be included in the bottom portion 8 of the housing underneath the sample strip 2. In some embodiments, the bottom portion 8 of the housing may also include a flow strip light guide port 13 positioned underneath the sample strip 2 for transmission-based detection methods.

FIG. 4 shows a top view of the bottom portion 8 of an exemplary cassette housing. As illustrated in FIG. 4, bottom portion 8 of the cassette housing includes flow strip light guide port 10, sample volume analysis port 12, flow strip light guide port 13, and one or more clamping regions 6. Additionally, the bottom portion 8 of the housing may also include a plurality of excess fluid channels 14 to remove excess liquid from the flow strips. Excess fluid channels 14 may be positioned on one or more sides of the flow strips, as shown in FIG. 4. In some example embodiments, excess fluid channels 14 may be formed between flow strips 2 and 7 (shown in FIG. 2). In these and other embodiments, excess fluid channels 14, at times also referred to as "capillary disruptors," may be formed on inner and/or outer sides of the sample strip 2 and/or the calibration strip 7 (shown in FIG. 2), as shown in FIG. 4. FIG. 4 shows an example cassette housing with capillary disruptors 14 formed on both inner and outer sides of sample strip 2 and calibration strip 7.

Figure 1:
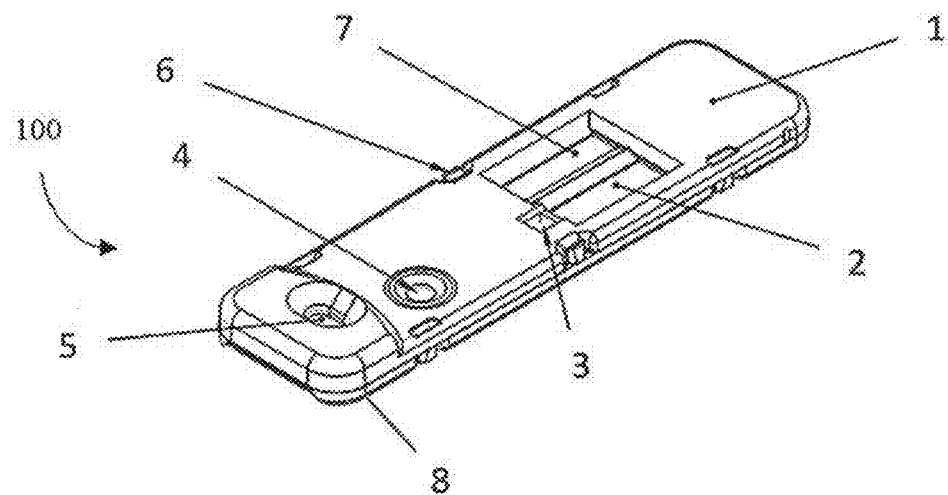
FIG. 1 shows a perspective view of an exemplary cassette that includes a calibration strip and a sample strip, in accordance with some embodiments of the subject disclosure.
Figure 2:
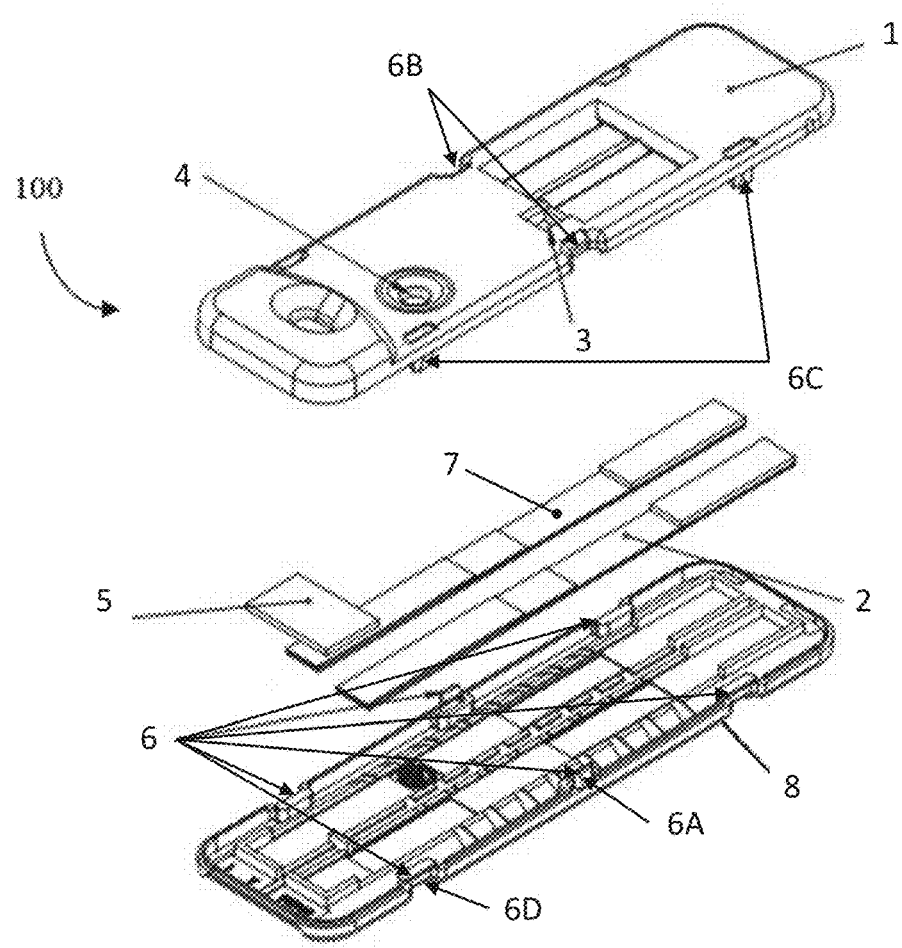
FIG. 2 shows an exploded view of the exemplary cassette shown in FIG. 1, in accordance with some embodiments of the subject disclosure.
Figure 3:
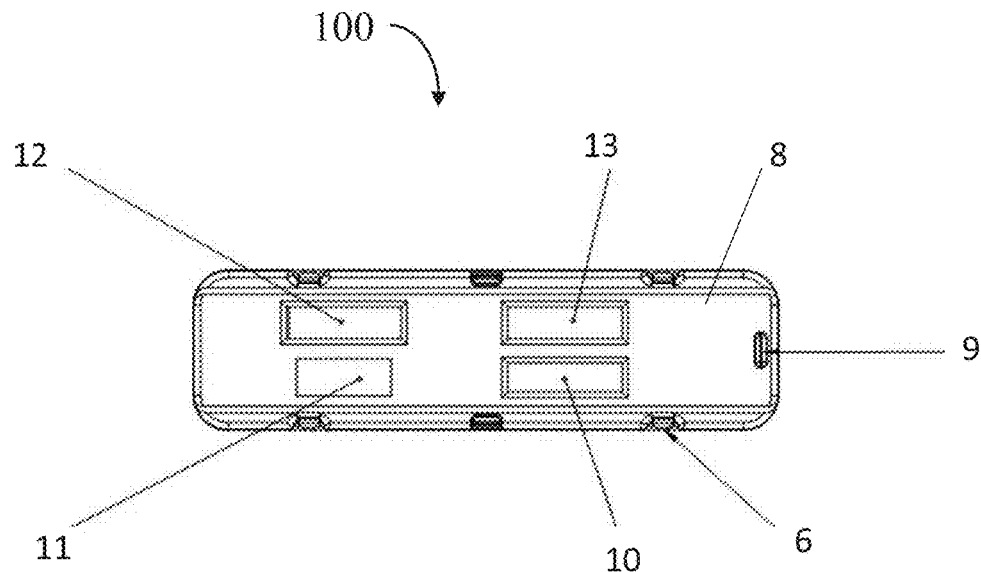
FIG. 3 shows a bottom view of an exemplary cassette shown in FIG. 1, in accordance with some embodiments of the subject disclosure.
Figure 4:
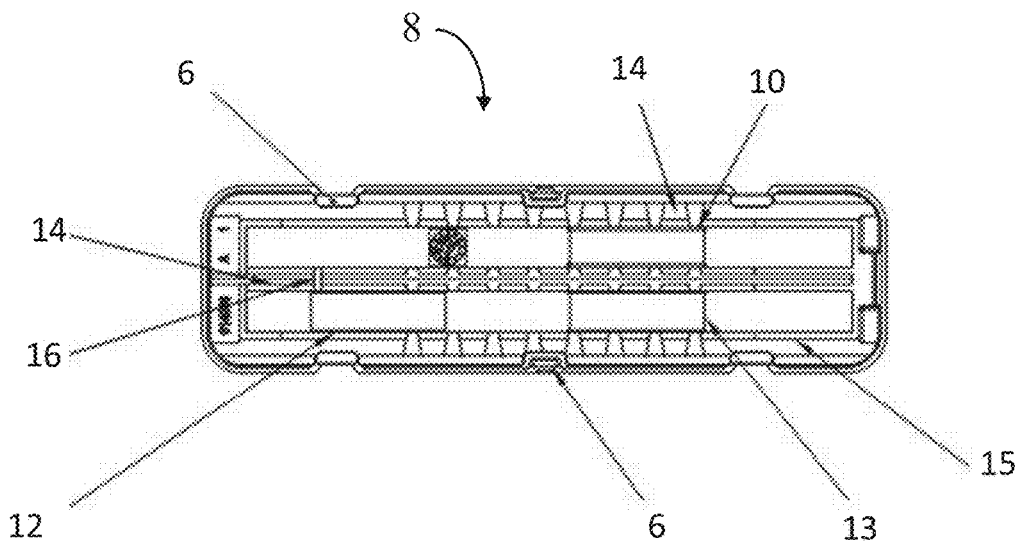
FIG. 4 shows a top view of the bottom portion of an exemplary cassette housing shown in FIG. 1, in accordance with an embodiment of the subject disclosure.

The bottom portion 8 of the cassette housing may also include side walls 15, which surround strips 2 and 7 (shown in FIG. 2). In some embodiments, side walls 15 may be lower in some regions to permit fluid from a flow strip (for example, a sample strip or calibration strip) to enter an excess fluid channel 14. In these and other embodiments, a fluid pad positioning bar 16 may also be formed in bottom portion 8 of the housing to facilitate proper positioning of a fluid pad.

Figure 5:
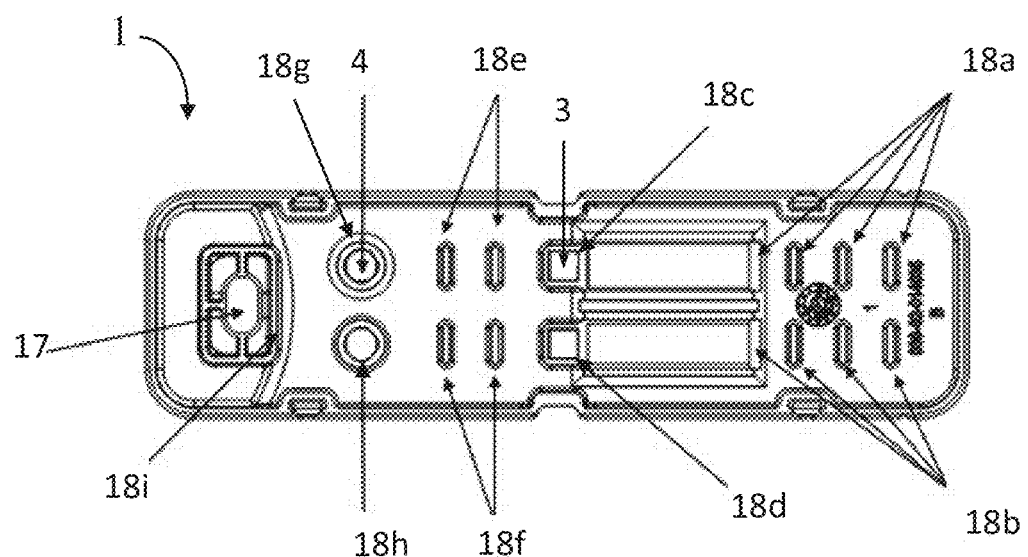
FIG. 5 shows an inside view of the top portion of an exemplary cassette housing shown in FIG. 1, in accordance with an embodiment of the subject disclosure.

FIG. 5 shows an inside view of the top portion 1 of an exemplary cassette housing. As shown, top portion 1 includes a fluid pad port 17 that provides fluid communication to both the sample strip 2 and the calibration strip 7 (shown in FIG. 2). Top portion 1 also includes a sample port 4 to allow sample to be introduced to a sample strip. In some embodiments, top portion 1 is configured to include a plurality of raised regions (referred to herein as "pressure points") that exert pressure on the sample strip 2 and/or the calibration strip 7.

In some embodiments, top portion 1 includes a plurality of pressure points 18, with an equal number of pressure points 18 in contact with sample strip 2 and calibration strip 7. FIG. 5 shows an example embodiment of the top portion 1 of the cassette that includes a plurality of pressure points 18. For example, pressure points 18a contact the sample strip 2 and pressure points 18b contact the calibration strip 7. Pressure point 18c surrounds wash port 3 above sample strip 2. In the example embodiment shown in FIG. 5, calibration strip 7 includes a pressure point 18d in the same shape as pressure point 18c, although no wash port is provided underneath. Having matching pressure points on both the calibration strip and sample strip can ensure that lateral flow progresses the same on both strips and the measurements obtained from the strips are comparable. Pressure points 18e are in contact with the sample strip 2 and pressure points 18f are in contact with calibration strip 7. To match the contact provided by a pressure point 18g surrounding sample port 4, top portion 1 of the housing may also include pressure point 18h, although no port is present in that location. As shown in FIG. 5, a pressure point 18i may be provided surrounding fluid pad port 17 that contacts both sample strip 2 and calibration strip 7.

FIG. 5 illustrates a cassette having seventeen pressure points (18a-18i), but it will be understood upon consideration of the subject disclosure that some example cassettes may include more or less pressure points than shown in FIG. 5. For example, in some embodiments, the top portion 1 of the cassette housing may include at least two, three, four, five, six, seven, or eight pressure points on each flow strip. In total, the top portion 1 of the housing may include any number of pressure points. For example, the top portion 1 may include between 2 and 30 pressure points, 5-25, or 10-20 pressure points. The example embodiment shown in FIG. 5 includes 17 pressure points, but embodiments with more or less pressure points are within the scope of the present disclosure. In various embodiments, at least one pressure point contacts both sample strip 2 and calibration strip 7. Additionally, the pressure points included on the top portion 1 of the cassette housing may be shaped as shown in FIG. 5, with linear, square, circular, and oval shapes, while, in other embodiments, other various other shapes or arrangements of shapes may be used.

Calibration Strip

Figure 6:
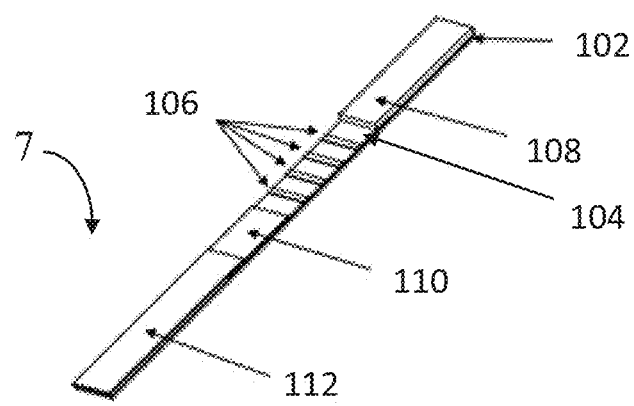
FIG. 6 shows a perspective view of an exemplary calibration strip configured in accordance with some embodiments of the subject disclosure.

FIG. 6 shows an exemplary calibration strip 7. The calibration strip 7 shown in FIG. 6 includes various substrates that permit capillary motion of fluid, affixed to an adhesive-lined backing 102. In some embodiments, backing 102 is formed of a polymeric material that is approximately as long as the calibration strip 7. In select embodiments, backing 102 is optically clear. In particular, backing 102 may permit transmission of at least 95% of visible light. A capillary flow substrate 104 may then be adhered to backing 102. Capillary flow substrate 104 may be formed of any suitable material, such as nitrocellulose or another porous material that permits fluid to flow via capillary action, such as nylon or polystyrene. In some embodiments, capillary flow substrate 104 extends along the entire length of backing 102 while in other embodiments, capillary flow substrate 104 is shorter than backing 102.

The capillary flow substrate 104 of calibration strip 7 may include marker regions 106 that include known concentrations of an analyte, a binding partner for the analyte, and/or a marker which, when bound to the analyte or to a binding partner bound to the analyte, emits a detectable signal. In some embodiments, the analyte on the calibration strip 7 is the same as the analyte of interest in the sample, while in other embodiments, the analyte on the calibration strip 7 is a control analyte that is distinct from the analyte of interest in the sample. In embodiments where a control analyte is used, the control analyte may be an analyte that binds to the same binding agents as the analyte of interest. The marker regions 106 may include appropriate components based on the design on the assay employed for the testing device. For example, if an example assay is designed to detect an antigen (as the analyte of interest), the assay may use an antibody as the binding partner and a gold particle as the marker. In some such embodiments, the marker regions 106 may include known quantities of antigen bound to antibody or known quantities of antigen and gold particles. In embodiments where the marker regions 106 include antigen bound to antibody, the gold particles may be included in a conjugate pad 110 and travel upwards to the marker regions 106 during the assay. Once the gold particles encounter the antigen bound to antibody, they may bond to form a complex. In embodiments where the marker regions 106 include antigen and gold particles, the conjugate pad 110 may include antibodies which travel upwards to the marker regions 106 during the assay and form a complex with the antigen and gold particles.

Numerous configurations and variations of the assay employed by the disclosed testing device are possible. For example, in some embodiments, the analyte of interest may be a receptor, hormone, antigen, antibody, protein, enzyme, DNA, RNA, vitamin, pharmaceutical substance, and/or environmental pollutant. In such cases, a suitable binding partner can be selected based on the identity of the analyte of interest. For example, suitable binding partners may be organic compounds, inorganic compounds, receptors, antigens, antibodies, hormones, enzymes, proteins, and/or DNA. Example markers beyond colloidal gold that may be used to bind to the analyte of interest directly or indirectly include but are not limited to: enzymes (such as horseradish peroxidase, alkaline phosphatase, or glucose oxidase), selenium, radioactive isotopes, DNA reporters, fluorogenic reporters (such as phycoerythrin), and/or electro chemiluminescent tags, inorganic compounds, such as silicon dioxide, ferric oxides, and chemical derivatives of inorganic compounds.

Additionally, the assay of the disclosed testing device may be competitive or non-competitive and may include one, two, or more binding sites. For example, the assay may be a one-site non-competitive assay in which the analyte binds with a marked binding partner (for example, a labelled antibody) and signal from the marked binding partners is measured to determine the concentration of analyte. In other embodiments, the assay may be a two-site non-competitive assay in which analyte binds to both a first binding partner (for example, an antibody site) and a marked binding partner (for example, a labelled antibody). This type of assay is commonly known as a "sandwich assay." In other embodiments, the assay may be a competitive assay, in which unmarked analyte competes with marked analyte to bind to a binding partner (for example, an antibody). The amount of marked, unbound analyte is then measured and used to calculate the concentration of (originally unmarked) analyte in the sample.

The example calibration strip 7 shown in FIG. 6 includes four distinct marker regions 106, but other embodiments may include at least two, at least three, four, five, or more marker regions 106. In some embodiments, the distinct marker regions 106 are each non-zero, while in other embodiments, at least one distinct marker region is zero. For example, in one embodiment, calibration strip 7 may include two distinct marker regions, with one being zero and the other being non-zero. In another example embodiment, calibration strip 7 may include two non-zero distinct marker regions. The marker regions 106 may be horizontal lines, as shown in FIG. 6, or may be non-linear. In some embodiments, each marker region 106 includes a different concentration of analyte and/or binding partner. In other embodiments, however, two of the marker regions 106 may include the same concentration of analyte and/or binding partner to evaluate deviations in measurement. For example, in some embodiments, the marker region 106 of a calibration strip includes analyte (with or without binding partner) in a concentration range of between 0 and 100%. In some embodiments, the marker region 106 of a calibration strip includes analyte concentrations that vary by more than 5%, more than 20%, or more than 50%. In one particular example embodiment, a calibration strip includes a first region with analyte in a concentration of 40%, a second region with analyte in a concentration of 60%, a third region with analyte in a concentration of 80%, and a fourth region with analyte in a concentration of 100%. In some embodiments, marker regions 106 may be arranged on calibration strip 7 such that fluid encounters regions with a lower analyte concentration prior to regions with a higher analyte concentration. Conversely, marker regions may be arranged such that fluid encounters regions with higher analyte concentration prior to regions with lower analyte concentration. Numerous configurations and variations will be apparent in light of the teachings provided herein.

As shown in FIG. 6, calibration strip 7 includes a conjugate pad 110, which is in contact with capillary flow substrate 104. In some embodiments, conjugate pad 110 may be positioned at least partially underneath or at least partially overlaying capillary flow substrate 104. Conjugate pad 110 may be formed of nitrocellulose or another porous material. In some embodiments, conjugate pad 110 may be loaded with appropriate materials for the assay, such as binding partners for the analyte of interest and/or markers. In some particular example embodiments, the conjugate pad contains dried detector antibodies bound to gold particles. When chase fluid is added via the fluid port 5 of the cassette 100, the fluid flows to both the calibration strip 7 and the sample strip 2, and the assay begins. The chase fluid may be any suitable fluid, such as water (for example, deionized water). In select embodiments, the chase fluid may include one or more buffers. The chase fluid mobiles or reconstitutes the compound(s) loaded on the conjugate pad 110. For example, if the conjugate pad includes dried detector antibodies bound to gold particles, the chase fluid will reconstitute the gold labeled detector antibody before continuing to flow up the capillary flow substrate 104. When the reconstituted gold labeled detector antibody reaches the antigen on the calibration strip, it binds to the antibody-antigen and forms a complex (antibody-antigen-Au-antibody), which produces signal.

In some embodiments, a sample pad 112 may be positioned on the calibration strip 7 at least partially overlapping conjugate pad 110. Sample pad 112 may be implemented with any appropriate material, such as nitrocellulose or another porous material. As described below in detail, sample strip 2 includes a sample pad onto which sample is deposited. In embodiments where sample strip includes a distinct sample pad, calibration strip 7 may also include a similarly-sized sample pad 112, as shown in FIG. 6.

Additionally, calibration strip 7 may also include an absorbent pad 108, as shown in FIG. 6, to collect excess fluid. Absorbent pad 108 overlaps capillary flow substrate 104 and may be formed of an absorbent material, such as nitrocellulose or other porous material. In some embodiments, one or more pressure points 18 on the top portion 1 of the cassette housing may be in contact with absorbent pad 108.

As will be understood by those skilled in the art upon consideration of the subject disclosure, calibration strip 7 may include fewer or more distinct portions than those shown in FIG. 6. In particular, FIG. 6 illustrates a calibration strip 7 that includes separate and distinct porous members for sample pad 112, conjugate pad 110, absorbent pad 108, and capillary flow substrate 104. However, in some embodiments, calibration strip 7 may be formed with fewer distinct porous members. For example, in some embodiments, calibration strip 7 may be formed with a single unitary porous member that includes regions corresponding to sample pad 112, conjugate pad 110, absorbent pad 108 and/or capillary flow substrate 104, in some embodiments. Numerous configurations and variations will be apparent to those skilled in the art.

Sample Strip

Figure 7:
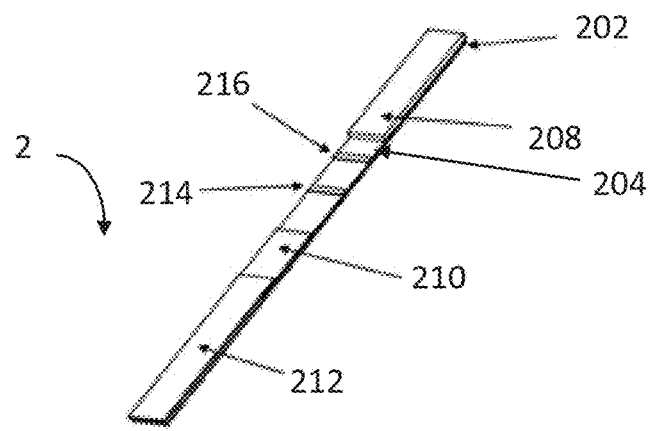
FIG. 7 shows a perspective view of an exemplary sample strip configured in accordance with some embodiments of the subject disclosure.

FIG. 7 illustrates an example sample strip 2 that includes backing 202, which may be the same or different from backing 102 of calibration strip 7, capillary flow substrate 204, which may be the same or different from capillary flow substrate 104, and absorbent pad 208, which may be the same or different from absorbent pad 108. In some circumstances, it may be advantageous to use the same materials in both the calibration strip and sample strip for the backing, capillary flow substrate, and absorbent pad to promote uniformity between the strips and ensure similar assay conditions. Sample strip 2 also includes a conjugate pad 210, which may be configured as described with respect to conjugate pad 110, and sample pad 212, which may be configured as described with respect to sample pad 112. In some embodiments, the material used for sample pad 112 of the calibrator strip 7 is the same material used for sample pad 212 of the sample strip 2.

As shown in FIG. 7, the sample strip 2 may include a test line 214 and a control line 216. Sample strip 2 may be configured such that fluid encounters test line 214 prior to control line 216 (as shown in FIG. 7) or such that fluid encounters control line 216 prior to test line 214. In some embodiments, control line 216 includes a known quantity of analyte (either analyte of interest or a control analyte) and the test line 214 includes one or more binding partners for the analyte of interest. In some embodiments, control line 216 may also include a binding partner for the analyte and/or a marker. For example, in one particular embodiment, the analyte of interest is an antigen and control line 216 includes known quantities of the antigen bound to an antibody. In this example embodiment, test line 214 also includes an antibody that will bind to analyte in the sample. The assay for this example cassette is performed using marker particles that travel from the conjugate pad and bind with the analyte complexes formed on the sample strip 2. In a different example embodiment, control line 216 includes known quantities of analyte and a marker. In this example embodiment, test line 214 includes marker particles and the assay is performed when the antibody binding partner travels to the test line 214 and control line 216 from the conjugate pad. Numerous variations for control line 216 and test line 214 will be apparent to one skilled in the art upon consideration of the subject disclosure.

Working Example 1

In a first example embodiment, a cassette includes a sample strip and a calibration strip designed to quantitatively test for Respiratory Syncytial Virus (RSV). The common lateral flow architecture for the sample strip and the calibration strip is as follows.

An example lateral flow strip was constructed using Lohmann Corporation adhesive backing plastic (0.010" White or clear polyester laminated with GL-187® acrylic PSA & supported with a release liner). Sartorius 25 mm CN140 Nitrocellulose was placed on top of the Lohmann backing material approximately 37 mm from the bottom of the backing material. 22 mm wide absorbent pad material CF5 from Whatman/GE was indexed with the top of the Lohmann backing material, creating an overlap onto the nitrocellulose and corresponding with pressure points of the cassette housing. On the lower side of the nitrocellulose a conjugate pad material is placed (14 mm Ahlstrom 6614, and/or Ahlstrom 1281 placed so that it creates an overlap on top of the nitrocellulose). A final 24 mm sample application material is indexed to the bottom of the Lohmann backing material to create an overlap onto the conjugate pad material. Once all components were assembled, the laminated material was then cut into 6 mm wide strips using a Biodot guillotine cutter. Additionally, a 10×15 mm fluid pad made from Ahlstrom 6614 was cut and placed over the bottom of the strips. To immunologically bind antigen, nitrocellulose is used to bind antibodies directed against the antigen of interest in the range of 50 pg/ml-3 mg/ml. A Biodot dispensing platform was used to accurately dispense four lines of antibody. The nitrocellulose was subsequently dried under forced hot air. With a second pass through the Biodot dispensing platform, antigen was dispensed on top of the antibody and subsequently dried. To create the increasing signal intensity ladder, increasing amounts of antigen (ng/mL) was used per line (lowest at the bottom). Detector antibody bound to gold particles from the same lot and concentration as the sample strip is applied to the conjugate pad material and dried.

The sample strip was constructed by depositing monoclonal anti RSV from Virostat Inc at 1.5 mg/mL onto Sartorius CN140 nitrocellulose using a Biodot dispensing system at a rate of 1 uL/cm. A goat anti chicken control line at 0.5 mg/mL was also deposited north of the RSV line at a rate of 1 uL/cm. Ahlstrom 1281 overlapped onto the nitrocellulose and Ahlstrom 6614 served as the sample/conjugate pad. A solution containing anti RSV from Virostat Inc conjugated to BBI 60 nm colloidal gold particles, and chicken IgY conjugated to BBI 40 nm colloidal gold particles were sprayed down onto the Ahlstrom 6614 using the Biodot dispensing system at a rate of 15 uL/cm and dried. Once laminated onto the Lohmann backing material, these strips were cut to 6 mm wide using the biodot cutter.

The calibration strip of this example embodiment was constructed as follows. Monoclonal anti RSV from Virostat Inc at 1.5 mg/mL was deposited into four evenly spaced lines onto Sartorius CN140 nitrocellulose using the Biodot dispensing platform and dried. With a second pass on the biodot dispensing platform, dilutions of RSV antigen positive control from Zeptometrix (40% on line 1, 60% on line 2, 80% on line 3 and 100% on line four) were deposited on top of the antibody lines and dried.

A chase fluid for the RSV reagents was prepared using Triton ×100, Tris buffer and Proclin 300. This solution was added to the fluid entry port after the sample was added.

Figure 8:
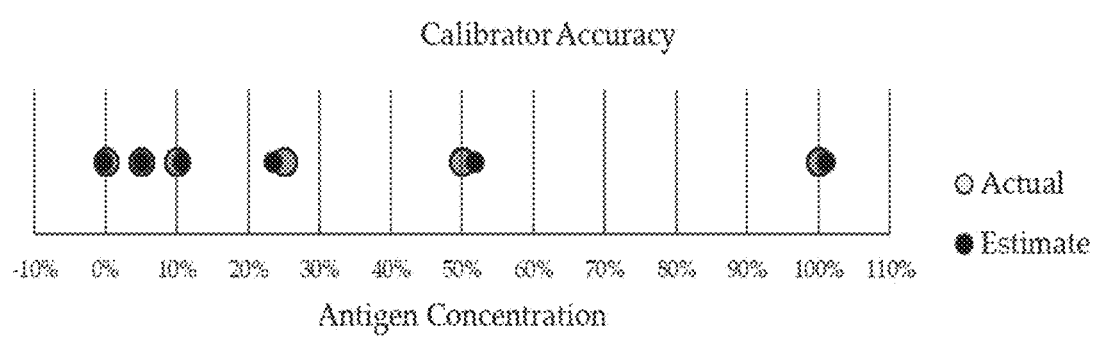
FIG. 8 shows a graphical representation of quantitative results obtained using an on-board calibrator for measuring Respiratory Syncytial Virus (RSV), in accordance with some example embodiments.

The described calibration and sample strips were assembled into a cassette along with a fluid pad. 20 uL of patient sample prepared from a nasal swab, nasal pharyngeal swab, nasal wash or viral transport media was added to the sample entry port. 300 uL of chase fluid was added to the fluid entry port. The cassette was then allowed to react at room temperature for 10 min. Signals from the four calibration lines on the calibration strip were recorded using a light reflectance lateral flow reader system from Detekt Biomedical and compared against unknown signals generated from the sample strip. Each cassette received its own calibration calculated from signals generated at the 10 min time point. Data obtained from this example was then compared to standards (dilutions of a positive control) to determine the accuracy of the cassette devices. Table 1 shows the results obtained. FIG. 8 shows a graphical representation of the results obtained using an on-board calibrator for measuring RSV.

TABLE 1

Accuracy of On-Board Calibrator for Measuring RSV

| Actual RSV Concentration | Measured RSV Concentration | Difference | % Difference |
|---|---|---|---|
| 0% | −.035% | 0.35% | N/A |
| 5% | 4.99% | 0.01% | 0.20% |
| 10% | 10.52% | 0.52% | 5.19% |
| 25% | 23.30% | 1.70% | 6.8% |
| 50% | 51.70% | 1.70% | 3.4% |
| 100% | 100.90% | 0.90% | 0.90% |

As shown in Table 1, the example testing device accurately predicted the percentage dilution of the positive control solution. Additionally, the largest difference recorded was less than a 7% error in measurement. In some embodiments, the quantitative measurement of the analyte concentration in the sample has an error percentage of less than 5%, 4%, 3%, 2%, or 1%.

Working Example 2

In another example embodiment, a kinetic lateral flow test was created to detect human thyroid stimulating hormone (TSH) levels in whole blood. The example testing device was constructed according to the following procedure. The calibration strip and sample strip were produced according to the common lateral flow architecture described in working example 1.

The sample strip was created by depositing monoclonal anti TSH (Biospacific) at 2 mg/mL onto 28 mm Sartorius CN140 nitrocellulose using a Biodot dispensing system at a rate of 1 uL/cm. A goat anti chicken control line at 0.5 mg/mL was also deposited north of the TSH line at a rate of 1 uL/cm. Ahlstrom 6614 (14 mm) overlapped the nitrocellulose and served as the conjugate pad material. A solution containing monoclonal anti TSH (Biospacific) conjugated to BBI 60 nm colloidal gold particles and chicken IgY conjugated to BBI 40 nm colloidal gold particles were sprayed down onto the Ahlstrom 6614 using the Biodot dispensing system at a rate of 15 uL/cm and dried. Once laminated onto the Lohmann backing material, these strips were cut to 6 mm wide using the Biodot cutter.

The calibration strip was constructed by depositing four evenly spaced lines of the same antibody and concentration used for the sample strip onto Sartorius CN140 nitrocellulose using the Biodot dispensing platform and dried. With a second pass on the biodot dispensing platform, TSH from Scripps Laboratories diluted into TSH free human serum (3.6 ng on line 1, 0.36 ng on line 2, 0.036 ng on line 3 and 0.0036 ng on line four) was deposited on top of the antibody lines and dried.

A chase fluid was developed to be compatible with the TSH reagents and to limit blood hemolysis. The chase fluid solution incorporated Tween 20, Sodium bicarbonate, and EDTA. This solution was added to the fluid entry port after the sample was introduced.

The example calibration and sample strips were assembled into the cassette along with a fluid pad. 20 uL of patient sample was added to the sample entry port and 200 uL of assay run fluid was added to the fluid entry port.

Figure 9:
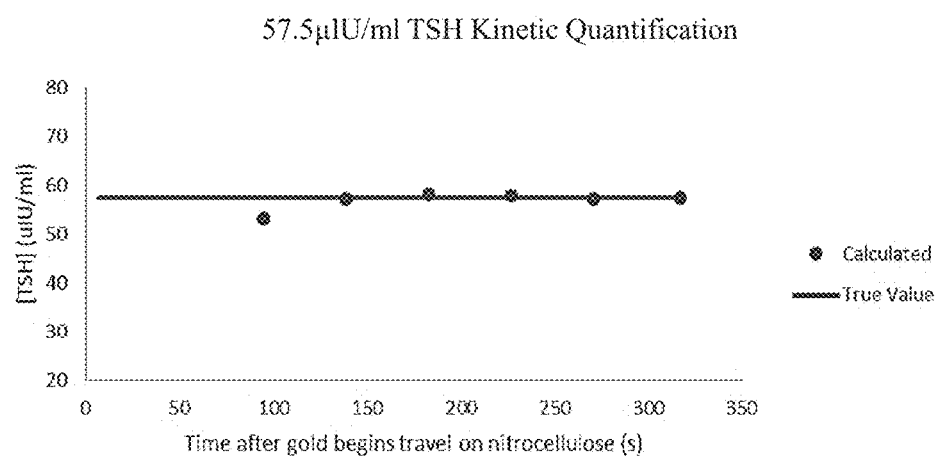
FIG. 9 shows a graphical representation of quantitative kinetic results obtained using an on-board calibrator for measuring thyroid stimulating hormone (TSH) at a concentration of 57.5 μIU/ml, in accordance with some example embodiments.
Figure 10:
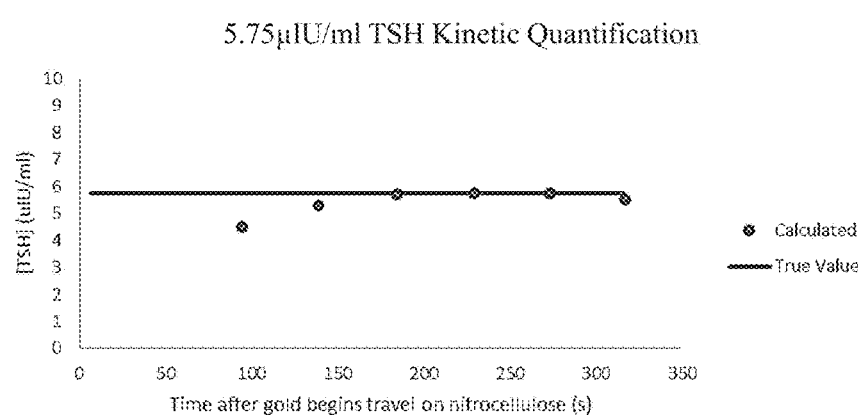
FIG. 10 shows a graphical representation of quantitative kinetic results obtained using an on-board calibrator for measuring TSH at a concentration of 5.75 μIU/ml, in accordance with some example embodiments.

The cassette was then inserted into a light transmission instrument (OIDx) which was capable of kinetically analyzing the cassette over time. Signals from the four calibration lines were recorded and compared against unknown signals generated from the sample. Each cassette received its own calibration calculated from signals generated at various time points. To determine the accuracy of the on-board calibration system, known standards were run as samples (Dilutions of World Health TSH standard). FIG. 9 shows the calculated concentration compared to the actual concentration as a function of assay time for the 57.5 µIU/ml sample and FIG. 10 shows the calculated concentration compared to the actual concentration as a function of assay time for the 5.75 µIU/ml sample.

Figure 11:
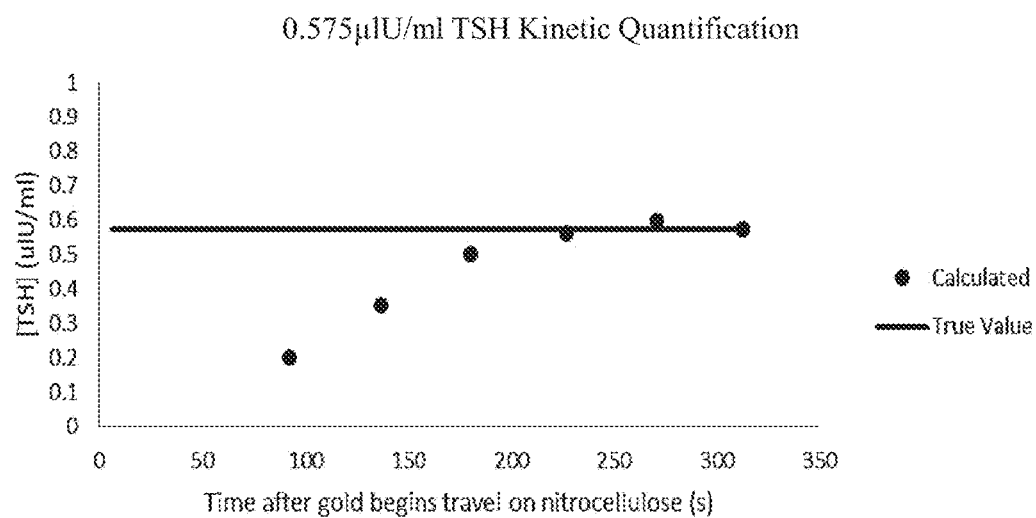
FIG. 11 shows a graphical representation of quantitative kinetic results obtained using an on-board calibrator for measuring TSH at a concentration of 0.575 μIU/ml, in accordance with some example embodiments.

As shown in FIG. 11, the 0.575 µIU/TSH sample, the value is reached within three minutes. In other embodiments, a lower standard of 0.0575 µIU/ml is used with similar results. By incorporating an assay stop function using accumulated signal on a control line, either located on the sample strip or the calibration strip, kinetic assays can be designed to produce values at the limit of detection (LOD) of an assay. For example, in the experiment above, if the LOD is 0.575 µIU/ml, the assay would be completed in three minutes. In some example embodiments, the LOD may be as low as 0.1 µIU/ml or 0.05 µI/ml. In some embodiments, the devices described herein are able to detect analyte at its LOD, for example, a concentration of 0.05 µIU/ml or less, within ten minutes after the chase fluid is introduced.

Working Example 3

In another example embodiment, a cassette was designed to detect human TSH levels in whole blood, which can cause background staining when used as a sample. The light transmission and sample volume analysis were also assessed. The calibration strip and sample strip were produced according to the common lateral flow architecture described in working example 1. The example cassette was constructed as follows.

The sample strip was prepared by depositing monoclonal anti TSH(Biospacific) at 2 mg/mL onto 28 mm Sartorius CN140 nitrocellulose using a Biodot dispensing system at a rate of 1 uL/cm. A goat anti chicken control line at 0.5 mg/mL was also deposited north of the TSH line at a rate of 1 uL/cm. Ahlstrom 6614 (14 mm) overlapped the nitrocellulose and served as the conjugate pad material. A solution containing monoclonal anti TSH(Biospacific) conjugated to BBI 60 nm colloidal gold particles and chicken IgY conjugated to BBI 40 nm colloidal gold particles were sprayed down onto the Ahlstrom 6614 using the Biodot dispensing system at a rate of 15 uL/cm and dried. Once laminated onto the Lohmann backing material, these strips were cut to 6 mm wide using the Biodot cutter.

Chase fluid was developed to be compatible with the TSH reagents and to limit blood hemolysis. The chase fluid solution incorporated Tween 20, Sodium bicarbonate, and EDTA. This solution was added to the fluid entry port after the sample was introduced. 25 uL of a highly hemolyzed whole blood sample was added to the sample port and then tested as normal. At nine minutes into the assay, the cassette was visually evaluated for problems due to hemolysis. Table 2 describes what was observed and how the wash port was used to clear up the background.

TABLE 2

Experimental Technique for Utilizing Wash Port

| Time (minutes) | Background Quality (after 9 min) | Treatment |
|---|---|---|
| 9:00 | Poor, red background | 10 uL of push buffer into the wash port |
| 9:10 | Immediate clearing at bottom of viewing window | Additional 10 uL of push buffer into the wash port |
| 9:20 | White background ⅓ up the strip | Additional 10 uL of push buffer into the wash port |
| 9:30 | White background over the test line | Additional 10 uL of push buffer into the wash port |
| 9:40 | White background over the control line | Additional 10 uL of push buffer into the wash port |
| 9:50 | White background over ¾ of strip | Additional 10 uL of push buffer into the wash port |
| 10:00 | White background over entire strip | Test read |

As shown in this example embodiment, the wash port can provide an effective way of clearing high background samples. Furthermore, the wash port is also amenable to automated practices. For example, in some embodiments, a cassette may be configured to automatically apply a solution via the wash port when background noise of a certain signal intensity is detected. Numerous implementation techniques will be apparent to one skilled in the art upon consideration of the subject disclosure.

Working Example 4

Figure 12:
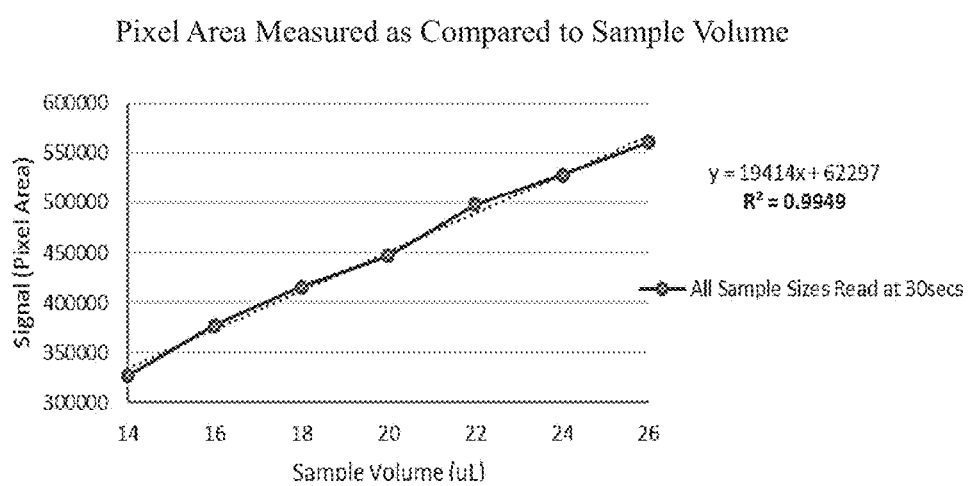
FIG. 12 shows a graphical representation of pixel area measured from an example cassette formed in accordance with some example embodiments, as a function of sample volume.
Figure 13:
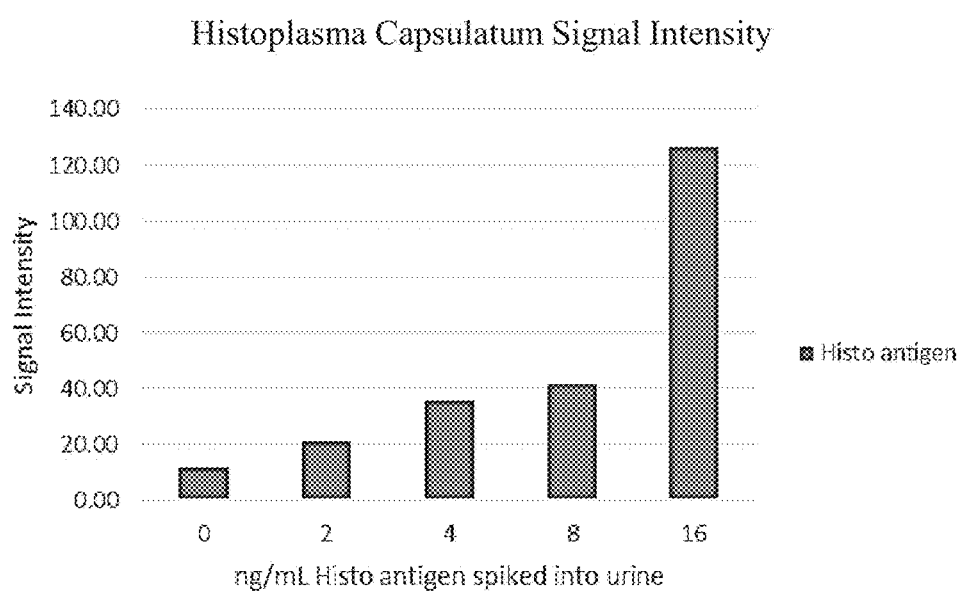
FIG. 13 shows a graphical representation of quantitative results obtained using an on-board calibrator for measuring *Histoplasma capsulatum*, in accordance with some example embodiments.

In another example embodiment, an instrument was created to measure light transmission and sample volume. This example instrument is referred to as "OIDx" herein. The OIDx instrument was programmed to measure pixel area from an image. To program the instrument, various amounts of whole blood were added to the sample port of an example cassette. An image of the strip was captured 30 seconds after the whole blood was added. FIG. 12 shows a graph of the signal measured (based on pixel area) as a function of the sample volume.

As can be seen in FIG. 12, the measured pixel area is linear between 14 µL and 26 µL of sample volume. The example light transmission instrument may, in some embodiments, eliminate the need to use a pipette for transferring sample volumes, such as blood from a finger prick. This may reduce further manipulative steps in the test procedure, thereby increasing the likelihood of obtaining CLIA-waved status by the FDA.

Working Example 5

In another example embodiment, a cassette was created to detect *histoplasma* in urine. The sample strip for the cassette was constructed using the common lateral flow architecture as previously described. To create the sample strip, rabbit monoclonal anti *Histoplasma Capsulatum* at 1.5 mg/mL was deposited onto 25 mm Sartorius CN140 nitrocellulose using a Biodot dispensing system at a rate of 1 uL/cm. A goat anti chicken control line at 0.5 mg/mL was also deposited north of the anti-*Histoplasma* line at a rate of 1 uL/cm. Ahlstrom 6614 overlapped the nitrocellulose and served as both the conjugate and sample pad. The Ahlstrom 6614 was treated prior to the depositing of colloidal gold to reduce interference with urine samples. A solution containing anti *Histoplasma* cap. conjugated to IMRA 40 nm colloidal gold particles and chicken IgY conjugated to IMRA 40 nm colloidal gold particles were sprayed down onto the Ahlstrom 6614 using the Biodot dispensing system at a rate of 15 uL/cm and dried. Once laminated onto the Lohmann backing material, these strips were cut to 6 mm wide using the Biodot cutter.

A chase fluid was developed to be compatible with the *Histoplasma* reagents and to limit interference from urine samples. The chase fluid solution incorporated Sodium Dodecyl Sulfate, Sodium Citrate and phosphate buffer. The described strip was placed into the cassette along with a fluid pad.

60 uL of urine spiked with known concentrations of *Histoplasma capsulatum* was added to the sample port. 300 uL of chase fluid was added to the fluid port and the assay was run for 10 minutes. Results were read on a Detekt Biomedical reader to quantitate signal. The data obtained is shown in FIG. 13. The data shown in FIG. 13 indicates that *Histoplasma capsulatum* can be detected in urine using the methods and devices described herein.

Additional Example Embodiments

The following additional example embodiments are provided to describe aspects of the presently disclosed methods and devices in further detail and are not intended to limit the scope of the subject disclosure.

In some example embodiments, a universal method for quantitative sample analysis is provided. The method may include, in some cases, a calibration curve obtained simultaneously with the sample analysis without additional user steps. In these and other embodiments, a lateral flow-based system can be achieved, where sample is added to an absorbent material which together with chase fluid reconstitutes dried colloidal gold antibody detector conjugates or other suitable detector binding agents. Through capillary force, the sample and colloidal gold detector moves laterally onto a controlled porosity membrane where binding partners such as antibodies, antigens, receptors and the like have been previously adsorbed onto the membrane. If analyte, i.e. antigen or antibody is present in the sample, a reaction occurs between the specific binding agents to produce a signal that can be read visually or quantitatively with an instrument and a calibration curve. This is commonly referred to as a 'sandwich assay,' where the analyte of interest is sandwiched between two suitable binding partners, one of which has a detector signal associated with the binding agent. The signal is directly proportional to the analyte concentration. In these and other embodiments, signals on the calibrator strip, which develop concurrent with the sample strip, are interpreted by an instrument to create a calibration or standard curve that the sample is compared to, thereby generating a quantitative result for the sample.

Techniques for creating a calibration curve (sometimes referred to as a 'standard curve') from measured signals are known to those skilled in the art. For example, measured signal may be plotted against analyte concentration and a best fit line may be generated between the data points. The best fit line may, in some cases, obey the equation $y=mx+b$, where y is the signal measured, m is the sensitivity (i.e., the slope of the line), x is analyte concentration, and b is a constant attributable to background. Once a best fit line is generated, unknown analyte concentrations can be determined using the equation. In some systems, the relationship between analyte concentration and signal measured may be linear or approximately linear within particular ranges of analyte concentration. The region where measured signal has a linear relationship to analyte concentration is referred to as the "linear range" herein. In some cases, the linear range may extend between the system's limit of detection (LOD) and the limit of linearity (LOL). Below the LOD, signal measured may be attributable to background interference and above the LOL, signal measured has a non-linear relationship to analyte concentration. Accordingly, measurements obtained between the LOD and the LOL (in the linear range) may produce a more reliable calibration curve than values outside the linear range.

As previously described, the disclosed devices include a calibration strip with particular analyte concentrations selected to produce signals to generate a reliable calibration curve to quantify analyte concentration in a solution that is applied to the sample strip. In some embodiments, the disclosed calibration strip includes at least one non-zero analyte concentration value. In these and other embodiments, the calibration strip may include a region with an analyte concentration of zero, from which signal is measured and then used to generate the calibration curve. In some particular example embodiments, only two signals read from the calibration strip (one from a region with a non-zero analyte concentration and another from a region with an analyte concentration of zero) may be used to generate a calibration curve. In some such example embodiments, the non-zero analyte concentration may be selected to be within the linear range to maximize accuracy. In these and other embodiments, the measured signal in a region with an analyte concentration of zero would correspond to the value of the "b" variable in the best fit line equation and would indicate signal produced from background and non-specific binding. Measuring signal from a region with an analyte concentration of zero may also be used in various embodiments to provide additional safety controls. For example, visual color developing in a region with zero analyte concentration may indicate a test failure and/or inaccuracy of results. Numerous configurations and variations will be apparent to those skilled in the art upon consideration of the subject dislcosure.

The disclosed cassettes may be compatible with an instrument capable of interpreting images either through light transmission or light reflectance. In some embodiments, a cassette may be read using light reflection and transmission-based detection methods. In embodiments where increased sensitivity is desired, light transmission can be used.

In some embodiments, the sample analysis results can be provided quantitatively. However, it is to be understood that in some embodiments, the quantitative results may be reported qualitatively, if desired. For example, in the case of TSH measurements, results may be reported as EUTHYROID, HYPERTHYROID, or HYPOTHYROID.

The disclosed methods may be used to monitor disease progression or regression with regard to medical treatment including prescriptions, in some embodiments. In some embodiments, the system may be used to monitor patient compliance with prescribed medications.

In various embodiments, the signals that develop are in addition to colloidal gold derived from nanomaterial-based Biosensors incorporating various detector strategies such as fluorescent labels, enzymes, chemiluminescence chemistries, ferromagnetic particles and silica particles.

In some cases, the quantitative result may be reported as a concentration of analyte mass per unit volume, an activity unit per unit volume or as a percentage of a reference value.

The disclosed cassettes can provide uniformity of liquid flow on both sample and calibration strips due to precision placement of pressure points within the device and suitable incorporation of barriers to ensure that migration or flow is absolutely restricted to the membrane strips. The disclosed systems can also utilize light reflection or transmission based detection with the same cassette and instrument. For certain tests such as a test for pregnancy where a number or quantitation is not required, the test can be read visually. In some embodiments, a wash port may be used to quantitate samples that feature hemolyzed whole blood or pigmented samples. The disclosed systems also may have the ability to remove interfering (false positives) particulates that may be present in certain samples by incorporating suitable membrane-based filters. The disclosed systems may also image and record the volume of sample added to the device, (for example a drop of blood from a finger prick, which would eliminate the need for accurate pipettes). Off-board mixing of colloidal gold and sample for added sensitivity and flexibility may be used in any of the disclosed assay designs.

In some embodiments, multiple sample types may be tested by the disclosed cassettes, including whole blood, urine, saliva, swabs, and/or fecal matter. With kinetic assay capability, the disclosed systems may report a result quickly (for example, within two to ten minutes), depending on sample concentration. The disclosed systems may have the ability to perform nucleic acid (PCR, rtPCR) assays and/or the ability to multiplex analytes on the same strip. The disclosed systems may also be compatible with colloidal gold, latex particles, fluorescent labels and superparamagnetic particles. In some embodiments, the calibration strip may feature a lot-specific calibrator which is referenced to a calibration curve performed at the date of manufacturing.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes, and not to limit the scope of the inventive subject matter described herein. The foregoing description of the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

What is claimed is:

1. A cassette configured to measure an analyte of interest, the cassette comprising:
   a calibration strip comprising a first region and a second region, the first region having a first concentration of an analyte and the second region having a second concentration of the analyte, wherein the first concentration is different from the second concentration;
   a sample strip positioned parallel to the calibration strip;
   a sample port in fluid communication with the sample strip but not in fluid communication with the calibration strip; and
   a fluid port in fluid communication with the calibration strip and the sample strip.

2. The cassette of claim 1, wherein the calibration strip further comprises a binding partner for the analyte in the first region and in the second region.

3. The cassette of claim 1, wherein the calibration strip further comprises a conjugate pad comprising a marker configured to bind with the analyte or a binding partner.

4. The cassette of claim 1, wherein the calibration strip further comprises a marker bound to or configured to bind to the analyte in the first region and in the second region.

5. The cassette of claim 4, wherein the calibration strip further comprises a conjugate pad comprising a binding partner for the analyte and/or the marker.

6. The cassette of claim 1, wherein the calibration strip further comprises a third region having a third concentration of the analyte that is distinct from the first concentration and the second concentration.

7. The cassette of claim 1, further comprising a wash port in fluid communication with the sample strip.

8. The cassette of claim 1, wherein the sample strip further comprises a control line comprising a known concentration of an analyte different from the analyte of interest and a test line comprising a binding partner for the analyte of interest.

9. The cassette of claim 1, wherein the first concentration of the analyte is zero and the second concentration of the analyte is greater than zero.

10. The cassette of claim 1, wherein the first concentration of the analyte is greater than zero and the second concentration of the analyte is greater than zero.

11. The cassette of claim 1, wherein the analyte of interest is a receptor, an antigen, an antibody, a hormone, a protein, an enzyme, DNA, RNA, a pharmaceutical substance, or an environmental pollutant.

12. The cassette of claim 1 further comprising a housing inside which the calibration strip and the sample strip are fixedly stored, wherein the housing contacts the sample strip in at least two locations and contacts the calibration strip in at least two locations.

13. The cassette of claim 12, wherein the housing contacts the sample strip in at least four locations and contacts the calibration strip in at least four locations.

14. A cassette comprising:
   a substantially rigid housing comprising a top portion and a bottom portion;
   a calibration strip fixedly retained in the housing, the calibration strip comprising a first region and a second region, the first region having a first concentration of an analyte and the second region having a second concentration of the analyte, wherein the first concentration is different from the second concentration;
   a sample strip fixedly retained in the housing;
   a sample port formed in the top portion of the housing above the sample strip, wherein the sample port is not in fluid communication with the calibration strip; and
   a fluid port formed in the top portion of the housing above both the calibration strip and the sample strip.

15. The cassette of claim 14, wherein the top portion of the housing further comprises a wash port formed in the top portion of the housing providing access to the sample strip.

16. The cassette of claim 14, wherein the bottom portion of the housing includes a sample volume analysis port underneath the sample strip or the sample port.

17. The cassette of claim 14, wherein the bottom portion of the housing includes a flow strip light guide port positioned underneath the sample strip and the calibration strip.

18. The cassette of claim 14, wherein the top portion of the housing includes a plurality of pressure points, wherein at least two pressure points are in contact with the sample strip and at least two pressure points are in contact with the calibration strip.

19. The cassette of claim 14 further comprising a plurality of excess fluid channels formed in the bottom portion of the housing, wherein one or more of the excess fluid channels are in fluid communication with the sample strip.

20. The cassette of claim 19, wherein one or more of the excess fluid channels are in fluid communication with the calibration strip.

* * * * *